United States Patent [19]

Weber et al.

[11] 4,016,156
[45] Apr. 5, 1977

[54] DISTYRYL COMPOUNDS

[75] Inventors: Kurt Weber, Basel; Geza Kormany, Allschwil, both of Switzerland

[73] Assignee: Ciba-Geigy Corporation, Ardsley, N.Y.

[22] Filed: Dec. 16, 1975

[21] Appl. No.: 641,319

Related U.S. Application Data

[63] Continuation of Ser. No. 374,141, June 27, 1973, abandoned.

[30] Foreign Application Priority Data

June 30, 1972 Switzerland .................. 9854/72

[52] U.S. Cl. .................. 260/240 D; 252/301.22; 252/543; 427/158
[51] Int. Cl.² .................. C07D 307/91
[58] Field of Search .......... 260/240 D; 252/543, 252/301.22; 427/158

[56] References Cited

UNITED STATES PATENTS

| 3,627,758 | 12/1971 | Weber et al. ............. | 260/240 D |
| 3,697,513 | 10/1972 | Siegrist ................... | 260/240 D |

OTHER PUBLICATIONS

Siegrist et al. Helvetia Chimica Acta 52 (1969) pp. 1282–1284, 1307.

*Primary Examiner*—Arthur P. Demers
*Attorney, Agent, or Firm*—Karl F. Jorda; Edward McC. Roberts; Prabodh I. Almaula

[57] ABSTRACT

New distyryl compounds of the formula

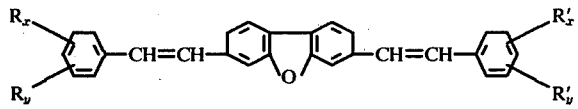

wherein $R_x$ denotes an optionally modified sulphonic acid group, a sulphone group, an optionally functionally modified carboxylic acid group or the nitrile group, $R_x'$ denotes an optionally functionally modified sulphonic acid group, a sulphone group, an optionally functionally modified carboxylic acid group, the nitrile group, alkyl, alkoxy, chlorine or hydrogen, and $R_y$ and $R_y'$, independently of one another, denote hydrogen, the sulphonic acid group or a salt thereof, chlorine, alkyl or alkoxy; these compounds are particularly useful as optical brighteners.

8 Claims, No Drawings

DISTYRYL COMPOUNDS

This is a continuation of application Ser. No. 374,141, filed on June 27, 1973, now abandoned.

The present invention relates to new 2,7-distyryl-dibenzofurane compounds, processes for their manufacture and their use as optical brighteners for high molecular organic materials.

The compounds according to the invention correspond to the formula

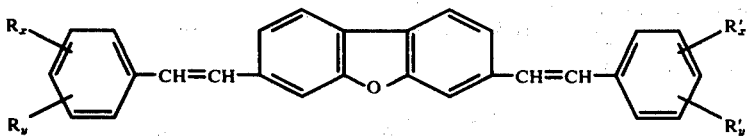

wherein $R_x$ denotes an optionally modified sulphonic acid group, a sulphone group, an optionally functionally modified carboxylic acid group or the nitrile group, $R_x'$ denotes an optionally functionally modified sulphonic acid group, a sulphone group, an optionally functionally modified carboxylic acid group, the nitrile group, alkyl, alkoxy, chlorine or hydrogen, and $R_y$ and $R_y'$ independently of one another denote hydrogen, the sulphonic acid group or a salt thereof, chlorine or alkyl.

Within the framework of the formula (1), symmetrically substituted compounds, that is to say those wherein $R_x = R_x'$ and $R_y = R_y'$, are of preferred interest. Compounds of this nature thus correspond in particular to the formula (2).

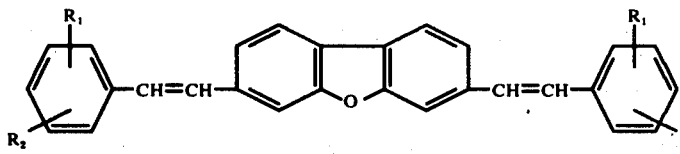

wherein $R_1$ denotes a sulphonic acid group, including its salts, a sulphonamide or sulphonic acid ester group, a carboxylic acid group, including its salts, a carboxylic acid ester group, the nitrile group, alkylsulphone or phenylsulphone and $R_2$ represents hydrogen, chlorine, alkyl with 1 to 4 carbon atoms, alkoxy with 1 to 4 carbon atoms or a sulphonic acid group, including its salts.

In both of the above formulae, $R_x$ and $R_x'$, or $R_1$ and $R_1'$, are preferably in the ortho-position to the ethylene bridge.

Amongst the salts of the sulphonic acid group or carboxylic acid group, the water-soluble types, such as the alkali metal salts, ammonium salts or amine salts, are of predominant importance. In certain cases, however, other salts for example barium salts, calcium salts or aluminium salts, can also be of interest. By the term "functionally modified" sulphonic acid group or carboxylic acid group there are above all to be understood the groups $-SO_2OX$,

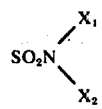

$-CO_2OX'$ and

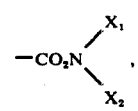

wherein X denotes optionally substituted phenyl, benzyl or alkyl with 1 to 18, especially 1 to 4, carbon atoms, X' denotes optionally substituted phenyl or benzyl, but preferably alkyl with 1 to 18, especially 1 to 4, carbon atoms, $X_1$ denotes hydrogen, alkyl with 1 to 18, preferably 1 to 4, carbon atoms which is optionally substituted by hydroxyl, halogen, alkoxy with 1 to 4 carbon atoms, nitrile, carboxyl, carbalkoxy with 2 to 8 carbon atoms, sulpho, amino or monoalkylamino or dialkylamino with 1 to 4 carbon atoms per alkyl part, cyclohexyl which is optionally substituted by methyl or phenyl or phenylalkyl (with 1 to 3 carbon atoms in the alkyl part) which are optionally substituted by halogen, methyl or methoxy, or $X_1$ together with $X_2$ and the nitrogen atom denotes optionally methyl-substituted morpholino, piperidino, pyrrolidino or hexamethyleneimino and $X_2$ denotes hydrogen, alkyl with 1 to 18, preferably 1 to 4, carbon atoms which is optionally substituted by hydroxyl, halogen, alkoxy with 1 to 4 carbon atoms, nitrile, carboxyl, carbalkoxy with 2 to 5 carbon atoms, sulpho, amino or monoalkylamino or dialkylamino with 1 to 4 carbon atoms per alkyl part, or $X_2$ together with $X_1$ and the nitrogen atom denotes optionally methyl-substituted morpholino, piperidino, pyrrolidino or hexamethyleneimino. Amongst the sulphone groups, alkylsulphone groups with 1 to 4 carbon atoms and phenylsulphone should be mentioned above all.

Compounds which deserve particular attention are those of the formula

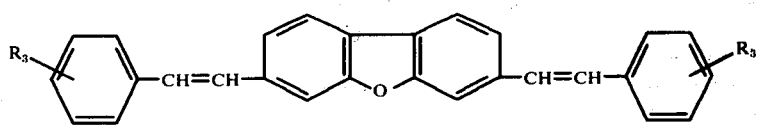

(3)

wherein $R_3$ denotes the sulphonic acid groups or their salts, aminosulphonyl, monoalkylaminosulphonyl or dialkylaminosulphonyl with 1 to 4 carbon atoms per alkyl part, phenoxysulphonyl, alkyloxysulphonyl with 1 to 4 carbon atoms, alkylsulphonyl with 1 to 4 carbon atoms, phenylsulphonyl, the carboxylic acid group or its salts, carbalkoxy with 2 to 8 carbon atoms, aminocarbonyl, monoalkylaminocarbonyl or dialkylaminocarbonyl with 1 to 4 carbon atoms per alkyl part or the nitrile group.

Compounds in which $R_3$ is in the ortho-position or metaposition to the ethylene bridge are preferred.

Further compounds to be singled out are those of the formula

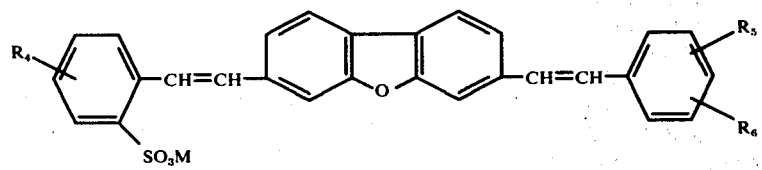

(4)

wherein $R_4$ denotes hydrogen, the sulphonic acid group or its salts, chlorine or methyl, $R_5$ denotes hydrogen, the sulphonic acid group or its salts, aminosulphonyl, monoalkylaminosulphonyl or dialkylaminosulphonyl with 1 to 4 carbon atoms per alkyl part, phenoxysulphonyl, alkoxysulphonyl with 1 to 4 carbon atoms, alkylsulphonyl with 1 to 4 carbon atoms, phenylsulphonyl, the carboxylic acid group or its salts, carboalkoxy with 2 to 5 carbon atoms, aminocarbonyl, monoalkylaminocarbonyl or dialkylaminocarbonyl with 1 to 4 carbon atoms per alkyl part or the nitrile group, $R_6$ denotes hydrogen, the sulphonic acid groups or its salts, chlorine, alkyl with 1 to 4 carbon atoms or alkoxy with 1 to 4 carbon atoms and M denotes a salt-forming cation.

Compounds of particular practical interest are the 2,7-distyryl-dibenzofuranes of the formula

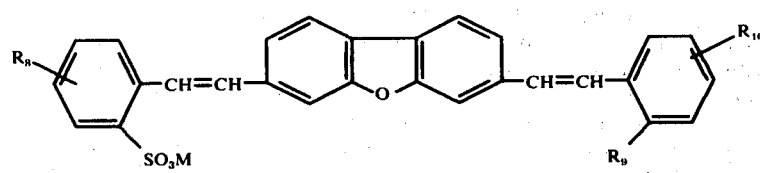

(5)

wherein $R_8$ represents hydrogen, chlorine, methyl or methoxy, $R_9$ represents hydrogen, the sulpho group or its salts, chlorine, methyl or methoxy, $R_{10}$ represents hydrogen, chlorine, methyl or methoxy and M represents a salt-forming cation.

The distyryl compounds of the formulae (1) to (5) can be manufactured analogously to methods which are in themselves known. In general, the procedure followed is that one mol of a compound of the formula

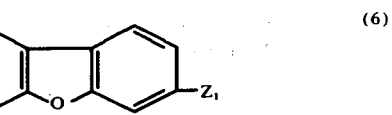

(6)

is reacted with one mol of a compound of the formula

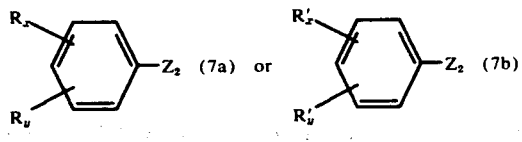

wherein one of the symbols $Z_1$ and $Z_2$ denotes a

and the other denotes a grouping of the formula

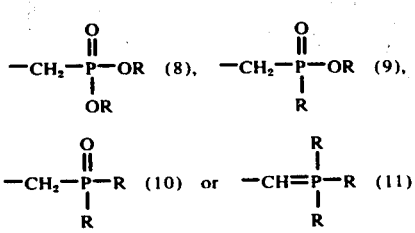

wherein R represents an alkyl radical which is optionally substituted further, preferably an alkyl radical with up to 6 carbon atoms, an aryl radical, preferably a phenyl radical, a cycloalkyl radical, preferably a cyclohexyl radical, or an aralkyl radical, preferably a benzyl radical, and that optionally further reactions are carried out at the substituents ($R_x$, $R_x'$, $R_y$ and $R_y'$).

Accordingly, it is possible for example, to react the dialdehyde of the formula

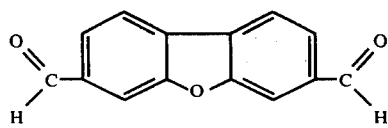

with monofunctional compounds of the formula

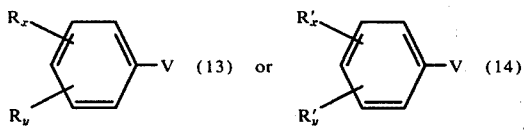

or monoaldehydes of the formula

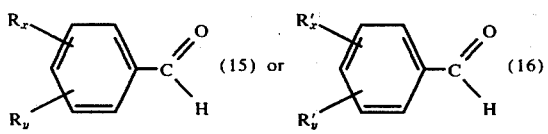

with the bifunctional compound of the formula

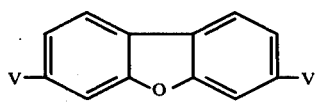

wherein $R_x$, $R_x'$, $R_y$ and $R_y'$ have the indicated meaning and V denotes one of the phosphorus-containing substituents of the formulae (8) to (11).

The phosphorus compounds of the formulae (13) or (14) and (17) which are required as starting substances are obtained when halogenomethyl compounds, preferably chloromethyl or bromomethyl compounds, of the formula

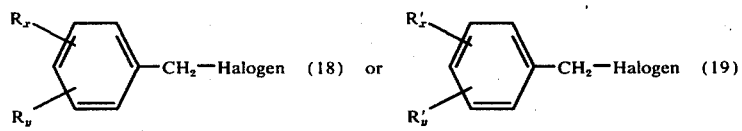

and

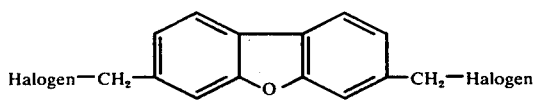

are reacted with phosphorus compounds of the formulae

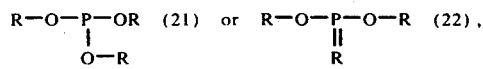

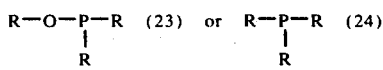

In these formulae R has the indicated meaning, and the radicals R bonded to oxygen are preferably lower alkyl groups whilst radicals R bonded directly to phosphorus are preferably aryl radicals such as benzene radicals.

Both the reactions for the manufacture of the starting substances and the reaction for the manufacture of the final substances can be carried out in the customary manner.

The reaction to manufacture the final substances is in both cases carried out by allowing the components to react in the presence of a strongly basic alkali compound and in the presence of a preferably hydrophilic strongly polar solvent, and in the case of the use of alkali metal hydroxides as the strongly basic alkali compound, these alkali metal hydroxides may contain up to 25% of water.

As examples of solvents for the process, described above, for the manufacture of compounds of the formulae (1) to (5) there may be mentioned toluene, xylene, chlorobenzene, alcohols such as, for example, ethanol and ethylene glycol monomethyl ether, but preferably N-methylpyrrolidone, dimethylformamide, diethylformamide, dimethylacetamide or dimethylsulphoxide.

The temperature at which the reaction is carried out can vary within wide limits. It is determined $\alpha$) by the stability of the solvent used towards the reactants, especially towards the strongly basic alkali compounds, $\beta$) by the reactivity of the condensation partners and $\gamma$) by the activity of the combination of solvent and base as a condensation agent. Preferably, the temperature lies approximately in the range of 30° to 60° C but in many cases satisfactory results can already be achieved at room temperature (about 20° C) on the one hand or, on the other hand, at temperatures of 100° C and even at the boiling point of the solvent, if this is desired for reasons of time saving or because a less active but cheaper condensation agent is to be used. In principle, reaction temperatures in the range of 10° to 180° C are thus also possible.

Possible strongly basic alkali compounds are above all the hydroxides, amides and alcoholates (preferably those of primary alcohols containing 1 to 4 carbon atoms) of the alkali metals, and for economic reasons, those of lithium, sodium and potassium are of predominant interest. However in principle, and in special cases, alkali metal sulphides and alkali metal carbonates, aryl-alkali metal compounds such as, for example, phenyl-lithium, or strongly basic amines (including ammonium bases, for example trialkylammonium hydroxides) can also be used with success.

Compounds according to the invention which contain functionally modified sulphonic acid groups or carboxylic acid groups can also be manufactured by the subsequent functional modification, carried out according to known processes, of the free sulphonic acid groups or carboxylic acid groups (or of their salts) of distyryldibenzofurane derivatives.

The new compounds defined above show a notable fluorescence in the dissolved or finely divided state. They can be used for the optical brightening of the most diverse synthetic, semi-synthetic or natural organic materials or of substances which contain such organic materials.

As such there may, for example, be mentioned the following groups of organic materials, where an optical brightening thereof is relevant, without the following survey being intended to express any restriction thereto: I. Synthetic organic high molecular materials:

a. Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example, polyamides of the polycaprolactam type, and also polymers which are obtainable both via polyaddition and via polycondensation, such as polyethers or polyacetals.

c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example alkyd resins) polyesters, polyamides (for example hexamethylenediamine adipate), maleate resins, melamine resins, their precondensates and analogues, polycarbonates and silicones, d. Polyaddition products such as polyurethanes (cross-linked and non-crosslinked) and epoxide resins.

II. Semi-synthetic organic materials, for example, cellulose esters of varying degrees of esterification (so-called 2 1/2 acetate or triacetate) or cellulose ethers, regenerated cellulose (viscose or cuprammonium cellulose), or their after-treatment products, and casein plastics. III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, say for example predominantly three-dimensional bodies such as sheets, profiles, injection mouldings, various machined articles, chips, granules or foams, and also as predominantly two-dimensional bodies such as films, foils, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboard or paper compositions.

The compounds to be used according to the invention are of importance, inter alia, for the treatment of organic textile materials, especially woven textile fabrics. Where fibres, which can be in the form of staple fibres or endless filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation, or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (coloured pigments or especially, for example, white pigments), or as an additive to dye baths, printing pastes, discharge pastes or reserve pastes, or for the after-treatment of dyeings, prints or discharge prints.

b. Mixed with so-called "carriers," wetting agents, plasticisers, swelling agents, anti-oxidants, light protection agents, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, antisoiling finishes or anti-static finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches".

f. As additives to the most diverse industrial products in order to render these more marketable (for example improving the appearance of soaps, detergents, pigments), g. In combination with other optically brightening substances, h. In spinning bath preparations, that is to say as additives to spinning baths such as are used for improving the slip for the further processing of synthetic fibres, or from a special bath before the stretching of the fibre.

i. As scintillators for various purposes of a photographic nature, such as, for example, for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 255° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetics, soluble salts of sulphonic acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerinesulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors," and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain for example: antistatic agents, skin protection agents which restore fat, such as lanolin, enzymes, antimicrobial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

thoxyphosphonomethyl)-dibenzofurane of the formula

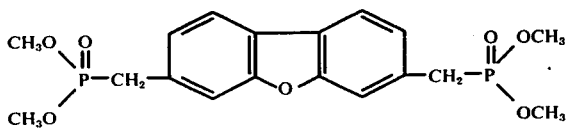

(27)

The washing treatment is carried out as follows, for example:

The textiles indicated are treated for 1 to 30 minutes at 20° to 100° C in a wash liquor which contains 1 to 10 g/kg of a built-up composite washing agent and 0.05 to 1%, relative to the weight of the washing agent, of the claimed brightening agents. The liquor ratio can be 1:3 to 1:50, After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples the parts, unless otherwise stated, are always parts by weight and the percentages are always percentages by weight. Unless otherwise noted melting points and boiling points are uncorrected.

EXAMPLE 1

A homogeneous mixture of 9.4 g of the sodium salt of benzaldehyde-2-sulphonic acid (approx. 88% pure) and 9.4 g of 2,7-bis-(diethoxy-phosphonomethyl)-dibenzofurane of the formula

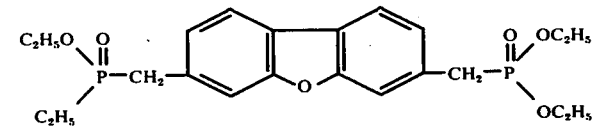

(25)

is introduced in portions, over the course of about 10 minutes, into a well-stirred suspension of 9.8 g of hydroxide hydroxide powder (approx. 91% pure) in 100 ml of dimethylformamide, whilst displacing the air by nitrogen. In the course of the introduction, the temperature rises from 24° to 40° C. The reaction mixture is then stirred for a further 2 hours at 40°–45° C and poured into 1,000 ml of desalinated water warmed to approx. 75° C, the mixture is cooled to approx. 25° C, neutralised with about 8 ml of concentrated hydrochloric acid and cooled to 25° C, and the product which has crystallised out is filtered off, washed with 200 ml of sodium chloride solution (300 g of NaCl dissolved in 1,000 ml of desalinated water) and recrystallised from a mixture of 100 ml of desalinated water and 100 ml of ethanol, with addition of 5 g of active charcoal. 8.5 g (73.8% of theory) of the compound of the formula can equally well be employed for the manufacture of the compound (26).

Equally, dimethylsulphoxide can be used as the solvent instead of dimethylformamide and sodium hydroxide powder can be used instead of potassium hydroxide powder. Finally, sodium methylate is also suitable for use at the alkaline condensation agent. 2,7-Bis-(diethoxyphosphono-methyl)-dibenzofurane of the formula (25) can be obtained as follows:

19.6 g of 2,7-dimethyldibenzofurane (manufactured according to Niementowski, Ber. 34, 3336 (1901)) are dissolved, together with 0.1 g of dibenzoyl peroxide in 400 ml of carbon tetrachloride at approx. 75° C. 35.6 g of N-bromosuccinimide together with 0.5 g of dibenzoyl peroxide are then introduced over the course of about 15 minutes. The mixture is stirred for a further 2½ hours at 70° – 75° C and allowed to cool to room temperature, and the product which has crystallised out is filtered off. The moist filter cake is boiled up in 800 ml of carbon tetrachloride, the undissolved succinimide is filtered off hot, the clear filtrate is cooled and the product which has crystallised out is filtered off and dried in vacuo at 70° – 80° C. 16.1 g of 2,7-bis-(bromomethyl)-dibenzofurane are thus obtained as a white crystal powder of melting point – –194° C. 15.0 g of 2,7-bis-(bromomethyl)-dibenzofurane are introduced into 100 ml of triethyl phosphite at – 140° C over the course of about 10 minutes whilst stirring. The mixture is then stirred for a further 2 hours at 135° – 140° C, in the course of which ethyl bromide distils off. The clear, light brown solution is cooled to 10° – 15° C and the product which crystallises out is filtered off, washed with about 250ml of hexane in portions and dried in vacuo at 60° – 65° C. 12.5 g (63.2% of theory) of 2,7-bis-(diethoxyphophonomethyl)-dibenzofurane of the formula (25) are thus obtained as a white crystal powder of melting point 86° – 87° C.

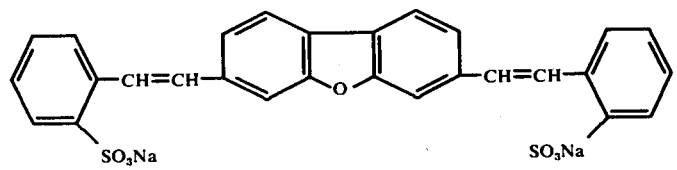

(26)

are obtained as a yellow powder.

Instead of the 2,7-bis-(diethoxyphosphonomethyl)-dibenzofurane of the formula (25) which was employed, the equivalent amount of the 2,7-bis-(dime-

EXAMPLE 2

5.6 g of 2,7-bis-(diethoxyphosphonomethyl)-dibenzofurane and 3.2 g of 3-cyanobenzaldehyde are dissolved in 50 ml of dimethylformamide at 35° to 40° C. 2.8 g of sodium methylate are added in portions over the course of 20 minutes to this solution whilst maintaining the temperature of the reaction mixture of 35° to 40° C. The reaction mixture is thereafter stirred for a further 2 hours at 35° to 40° C and is then cooled to 10° C. The product obtained is filtered off and boiled up with water, filtered off hot and recrystallised from a mixture of 400 ml of dioxane, 100 ml of benzene and a little active charcoal. 2.1 g of the compound of the formula

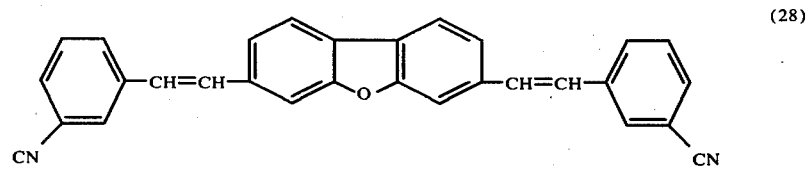
(28)

are obtained as a light yellow powder of melting point 256° to 258° C.

EXAMPLE 3

4.7 g of 2,7-bis-(diethoxyphosphonomethyl)-dibenzofurane and 3.2 g of 2-carboxybenzaldehyde are dissolved in 50 ml of dimethylformamide. The solution is heated to 35° – 40° C. 2.5 g of sodium methylate are then added in portions over the course of 20 minutes. The reaction mixture is stirred for a further 2 hours at 35° to 40° C and is then left to stand for 12 hours at room temperature. The small amount of a precipitate produced is filtered off and the filtrate is completely evaporated on a rotary evaporator. 13.7 g of a viscous, dark yellow mass are left and are dissolved in 50 ml of hot distilled water to which 2.8 g of sodium carbonate have been added. This solution is evaporated to dryness on a rotary evaporator. The resulting sticky mass is suspended in 550 ml of chlorobenzene. The suspension is warmed to 95° C and 16 g of dimethyl sulphate are added. After the reaction mixture has been stirred for 1 hour at 95° C, a further 16 g of dimethyl sulphate are added, the whole is stirred for 18 hours at 95° C and a further 16 g of dimethyl sulphate are added. The whole is stirred for a further 3 hours at 95° C and is then filtered hot.

From the filtrate, the by-product is isolated by column chromatography using a solvent mixture of toluene-ethyl acetate, 8:2, and the main product using toluene-ethyl acetate, 7:3. After recrystallisation from benzene, 10.3 g of the compound of the formula

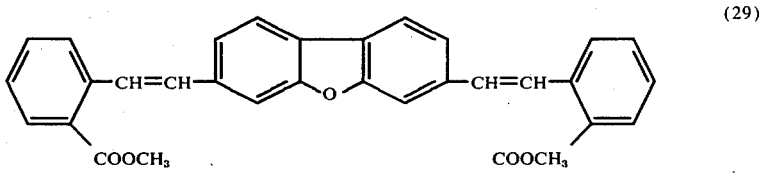
(29)

are obtained as a light yellow powder of melting point 157° to 158° C.

EXAMPLE 4

16.3 g of the compound of the formula (26) are suspended in 200 ml of chlorobenzene. The suspension is warmed to 65° C and a few drops of dimethylformamide are added, followed by 27 ml of thionyl chloride added dropwise over the course of 20 minutes. The reaction mixture is thereafter stirred for 2½ hours at 65° to 70° C and then cooled to 10° C and filtered. The resulting yellow precipitate is boiled up in 80 ml of chlorobenzene. The white precipitate which remains is filtered off hot. On cooling, 10.5 g of the sulphochloride of the compound of the formula (26), of melting point 223° to 226° C, crystallise out from the filtrate. 5.5 g of this sulphochloride are suspended in 500 ml of benzene. Dimethylamine gas is passed into the suspension, warmed to 70° C. After about one hour, a slightly turbid solution is produced. Thereafter, dimethylamine is passed in for a further hour. A yellow suspension is produced, which is stirred for a further hour at 70° C, then cooled in an ice bath and thereafter filtered. The residue, a yellow powder, is boiled up in 1 N sodium carbonate solution, filtered off hot and well washed with water.

After recrystallisation from 250 ml of methylcellosolve and active charcoal, 2.4 g of the compound of the formula

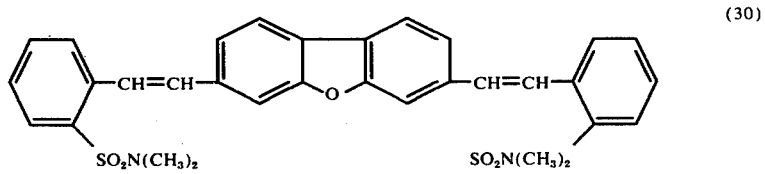
(30)

are obtained in the form of light yellow flakes of melting point 238° to 239° C.

EXAMPLE 5

The following compounds of the general formula

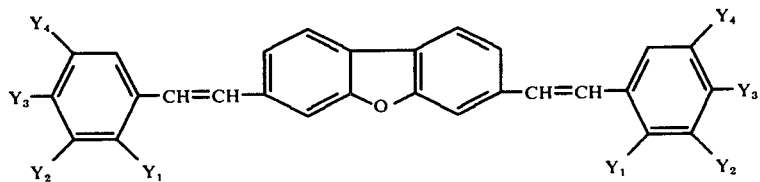
(31)

were obtained anlogously to the description in Examples 1 to 4:

g of a yellow crystal powder, fluorescing green-yellow in UV light, of the compound of the formula

| Compound of the formula | $Y_1$ | $Y_2$ | $Y_3$ | $Y_4$ | Melting point |
|---|---|---|---|---|---|
| (32) | H | $SO_3Na$ | H | H | >300° C |
| (33) | COOH | H | H | H | >300° C |
| (34) | $SO_2N\diagup O$ | H | H | H | 273–274° C |
| (35) | $SO_2N(CH_2CH_2OH)_2$ | H | H | H | 205–206° C |
| (36) | H | H | $SO_2CH_3$ | H | >300° C |
| (37) | H | H | COOH | H | >300° C |
| (38) | H | H | $COOCH_2$ | H | 185–187° C |
| (39) | H | H | $CON\diagup CH_3 \diagdown CH_3$ | H | 198–199° C |
| (40) | $SO_3Na$ | H | H | $SO_3Na$ | >300° C |
| (41) | $SO_3Na$ | H | $SO_3Na$ | H | >300° C |

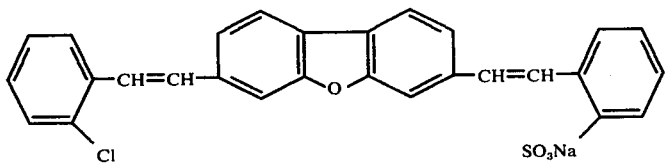
(42)

are thus obtained.

EXAMPLE 6

8.7 g of sodium salt of benzaldehyde-2-sulphonic acid (92% pure), 8.4 g of 2-chlorobenzaldehyde and 18.7 g of bis-(diethoxy-phosphono-methyl)-dibenzofurane are suspended in 200 ml of anhydrous dimethylformamide and a mixture of 3.2 g of potassium hydroxide and 2.8 g of sodium methylate (97% pure) is introduced in portions over the course of 40 minutes at 30° C, whilst stirring well. Thereafter the mixture is stirred for a further 3 hours at 40° C. The reaction mixture, which fluoresces blue, is evaporated to dryness with silica gel and the by-product is eliminated with a solvent mixture of toluene-ethyl acetate, 7:3, and the main product using ethyl acetatemethanol, 7:3, as the flow agent. As the purification process progresses, thin layer chromatography on silica gel plates provides valuable aid; the system ethyl acetate-methanol, in the volume ratio of 7:3, can be used, for developing the plate. 20.1

EXAMPLE 7

The procedure according to Example 6 is followed but the 2-chlorobenzaldehyde is replaced by 8.2 g of 3-methoxybenzaldehyde. After evaporation of the reaction mixture, a crystal paste is obtained. The crude product is recrystallised from dimethylformamide-water. 12.6 g of the compound of the formula

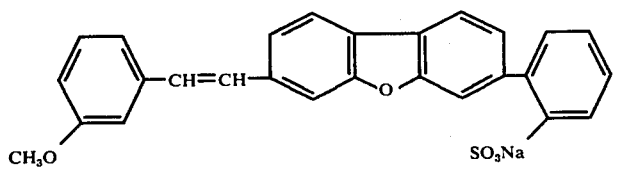
(43)

are obtained as a light yellow crystal powder of melting point above 280° C (with decomposition).

EXAMPLE 8

If the aldehyde reaction components mentioned in Example 6 are replaced by those listed in column 1 and 2 of Table I below, and in particular in the quantity ratios indicated therein, and in other respects the procedure noted in Example 6 or Example 7 respectively, is followed, the compounds indicated, with their yields, in column 3 are obtained.

Table I

| 1 | 2 | Compound of the formula | 3 |
|---|---|---|---|
| CH₃-C₆H₃(CHO)(CH₃) (2,3-dimethylbenzaldehyde type)  6.0 g | CHO, CO₃Na substituted benzaldehyde  8.7 g | (44) | CH₃-aryl-CH=CH-[dibenzofuran]-CH=CH-aryl-SO₃Na (with CH₃)  10.6 g  Melting point > 300° C |
| phenyl-SO₂-phenyl-CHO  10.4 g | CHO, SO₃Na substituted toluene  8.7 g | (45) | phenyl-SO₂-phenyl-CH=CH-[dibenzofuran]-CH=CH-phenyl-SO₃Na  11.7 g  Melting point > 300° C |
| CHO, COOCH₃ benzene  6.4 g | CH₃, CHO, CH₃ benzene  6.0 g | (46) | CH₃OCO-aryl-CH=CH-[dibenzofuran]-CH=CH-aryl(CH₃)(CH₃)  12.8 g  Melting point 190 to 191° C |

EXAMPLE 9

Bleached cotton fabric is washed for 15 minutes, using a liquor ratio of 1:20, in a liquor at 50° C which contains the following additives per liter:

- 0.004 g of the brightener of the formula (26), (32) or (42)
- 0.25 g of active chlorine (liquid bleach)
- 4 g of a washing powder of the following composition:
  - 15.00% of dodecylbenzenesulphonate
  - 10.00% of sodium lauryl-sulphonate
  - 40.00% of sodium tripolyphosphate
  - 25.75% of anhydrous sodium sulphate
  - 7.00% of sodium metasilicate
  - 2.00% of carboxymethylcellulose
  - 0.25% of ethylenediaminetetraacetic acid The cotton fabric is only introduced into the bath 15 minutes after preparing the washing bath which is at 50° C. After rinsing and drying, the fabric shows a good brightening effect of good fastness to acid, light and chlorine.

A good brightening effect is also obtained if the washing process is carried out in the same manner for 15 minutes at 25° C.

The washing powder of the abovementioned composition can also be directly incorporated into the brightener of the formula (26), (32) or (42).

EXAMPLE 10

A polyamide fibre fabric (Perlon) is introduced, using a liquor ratio of 1:40, into a bath at 60° C which contains (relative to the fabric weight) 0.05% of a brightener of the formula (26), (32), (34), (35), (39) or (43) and, per liter, 1 g of 80% strength acetic acid and 0.25 g of an addition product of 30 to 35 mols of ethylene oxide to one mol of technical stearyl alcohol. The mixture is warmed to the boil over the course of 30 minutes and is kept at the boil for 30 minutes. After rinsing and drying, a good brightening effect is obtained.

If instead of the polyamide-6 fabric a polyamide-66 (nylon) fabric is used, similar brightening effects are obtained.

Finally, it is also possible to work under high temperature conditions, for example for 30 minutes at 130° C. For this type of use, it is advisable to add 3 g/l of hydrosulphite.

EXAMPLE 11

10,000 g of a polyamide in chip form, manufactured in a known manner from hexamethylenediamine adipate, are mixed for 12 hours with 30 g of titanium dioxide (rutile modification) and 5 g of the compound of the formula (26), (45) or (46) in a tumbling vessel. The chips treated in this way are fused in a kettle, heated to 300° – 310° C with oil or diphenyl vapour, after the atmospheric oxygen has been displaced by steam, and the fused material is stirred for half an hour. Thereafter the melt is extruded under a nitrogen pressure of 5 atmospheres gauge through a spinneret and the filament spun in this way and cooled is wound up on a spinning bobbin. The filaments produced show a good brightening effect.

If instead of a polyamide manufactured from hexamethylenediamine adipate a polyamide manufactured from ε-caprolactam is used, similarly good results are obtained.

EXAMPLE 12

Bleached woolen fabric is treated, using a liquor ratio of 1:40, for 60 minutes in a bath which contains 0.1% of the brightener of the formula (26), (40), (41) or (44), relative to the fibre weight, and 4 g/l of hydrosulphite. After rinsing and drying, strong brightening effects of good fastness to light are obtained.

Strong brightening effects are also obtained if instead of the hydrosulphite, 5% of acetic acid, calculated relative to the fibre weight, are added to the bath.

EXAMPLE 13

Bleached cotton fabric is washed, using a liquor ratio of 1:20, for 30 minutes at 95° C. The washing liquor contains the following additives per liter:
  0.004 g of the brightener of the formula (26), (32) or (33)
  4 g of a washing powder of the following composition:
    40.0% of soapflakes
    15.0% of sodium tripolyphosphate
    8.0% of sodium perborate
    1.0% of magnesium silicate
    11.0% of sodium metasilicate (9 $H_2O$)
    24.6% of calcined sodium carbonate
    0.4% of ethylenediaminetetraacetic acid.

After rinsing and drying, the cotton fabric shows a strong brightening effect.

EXAMPLE 14

A polyester fabric (based on terephthalic acid-ethylene glycol) is padded at room temperature with an aqueous dispersion which contains, per liter, 2 g of the compound of the formula (29) or (38) and 1 g of an addition product of about 8 mols of ethylene oxide to 1 mol of p-tert.-octylphenol, and is dried at about 100° C. The dry material is subsequently briefly subjected to a heat treatment at 220° C. The material treated in this way shows a strong brightening effect of good fastness to light.

If, instead of the polyester fabric described above, a polyester fabric manufactured by co-condensation with 2 to 5 mol% os isophthalic acid-5-sodium sulphonate (Dacron 64) is used, a strong brightening of good fastness to light is again obtained.

EXAMPLE 15

100 parts of a granular polyester of terephthalic acid-/ethylene glycol are intimately mixed with 0.05 part of one of the compounds of the formulae (29), (36) or (38) and the mixture is fused at 285° C, whilst stirring. After spinning the spinning composition through customary spinnerets, strongly brightened polyester fibres are obtained.

EXAMPLE 16

A casting composition of 10 g of polyacrylonitrile, 0.2 g of titanium dioxide (anatase modification) as the delustering agent and 40 ml of dimethylformamide, containing 5 mg of the compound of the formula (29), is cast on a glass plate and spread by means of a metal rod to give a thin film. After drying, the film is strongly brightened.

EXAMPLE 17

An intimate mixture of 100 parts of polyvinyl chloride, 3 parts of stabiliser (Advastat BD 100: Ba/Cd complex), 2 parts of titanium dioxide, 59 parts of dioctyl phthalate and 0.01 to 0.2 part of one of the compounds of the formulae (28), (29) or (38) is milled on a calendar at 150° to 155° C to give a film. The opaque polyvinyl chloride film thus obtained has a substantially higher degree of whiteness than a film which does not contain the optical brightener.

EXAMPLE 18

100 parts of polystyrene and 0.1 part of one of the compounds of the formula (28) or (29) are fused with exclusion of air for 20 minutes at 210° C in a tube of 1 cm diameter. After cooling, an optically brightened polystyrene mass of good fastness to light is obtained.

EXAMPLE 19

1,000 parts of granular polyamide-6 are mixed for 12 hours in a tumbler vessel with 3 parts of titanium dioxide (rutile modification) and 1 part of one of the compounds of the formulae (33), (34), (35) or (39). The mixture is fused whilst excluding atmospheric oxygen and the melt is spun in the usual manner. The filaments obtained are strongly brightened.

What we claim is:

1. Distyryl-dibenzofuranes of the formula

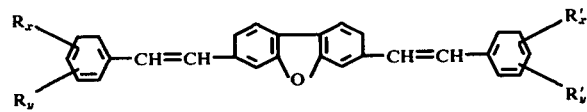

wherein $R_x$ is selected from the group consisting of sulphonic acid, benzyl ester of sulphonic acid, phenylester or alkylester of sulphonic acid with 1 to 18 carbon atoms in the alkyl part, alkylsulphone of 1 to 4 carbon atoms, phenylsulphone, a sulphonamide, a carboxylic acid, a carboalkoxy of 2 to 9 carbon atoms or a nitrile, $R_x'$ is selected from the group consisting of sulphonic acid, benzylester of sulphonic acid, phenylester or alkylester or sulphonic acid with 1 to 18 carbon atoms in the alkyl part, alkylsulphone of 1 to 4 carbon atoms, phenylsulphone, a carboxylic acid, a carboalkoxy of 2 to 9 carbon atoms, nitrile, alkyl of 1 to 4 carbon atoms, alkoxy of 1 to 4 carbon atoms, chlorine or hydrogen, and $R_y$ and $R_y'$ independently of one another are hydrogen, sulphonic acid or a salt thereof, chlorine, alkyl of 1 to 4 carbon atoms or alkoxy of 1 to 4 carbon atoms.

2. Distyryl-dibenzofuranes according to claim 1, corresponding to the formula

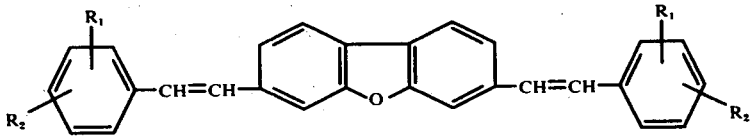

wherein $R_1$ is selected from the group consisting of sulphonic acid or its salts, a sulphonamide, benzylester of sulphonic acid, phenylester or alkylester of sulphonic acid with 1 to 4 carbon atoms in the alkyl part, carboxylic acid or its salts, carboalkoxy of 2 to 9 carbon atoms, nitrile, alkylsulphone of 1 to 4 carbon atoms or phenylsulphone, and $R_2$ is selected from the group consisting of hydrogen, chlorine, alkyl with 1 to 4 carbon atoms, alkoxy with 1 to 4 carbon atoms or a sulphonic acid or its salts.

3. Distyryl-dibenzofuranes according to claim 1, corresponding to the formula

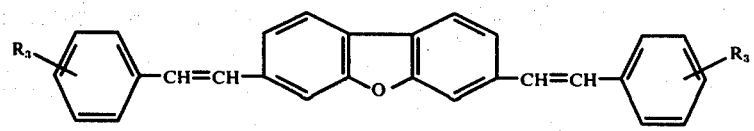

wherein $R_3$ is selected from the group consisting of sulphonic acid or its salts, aminosulphonyl, monoalkylaminosulphonyl or dialkylaminosulphonyl with 1 to 4 carbon atoms per alkyl part, phenoxysulphonyl, alkyloxysulphonyl with 1 to 4 carbon atoms, alkylsulphonyl with 1 to 4 carbon atoms, phenylsulphonyl, carboxylic acid or its salts, carboalkoxy with 2 to 9 carbon atoms, aminocarbonyl, monoalkylaminocarbonyl or dialkylaminocarbonyl with 1 to 4 carbon atoms per alkyl part or nitrile.

4. Distyryl-dibenzofuranes according to claim 1, corresponding to the formula

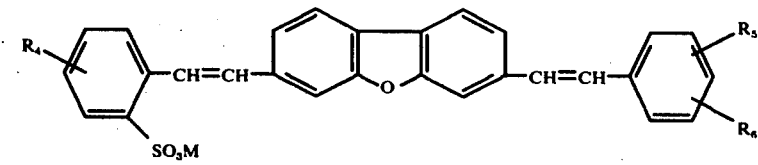

wherein $R_4$ is selected from the group consisting of hydrogen, sulphonic acid or its salts, chlorine or methyl, $R_5$ is selected from the group consisting of hydrogen, sulphonic acid or its salts, aminosulphonyl, monoalkylaminosulphonyl or dialkylaminosulphonyl with 1 to 4 carbon atoms per alkyl part, phenoxysulphonyl, alkoxysulphonyl with 1 to 4 carbon atoms, alkylsulphonyl with 1 to 4 carbon atoms, phenylsulphonyl, carboxylic acid or its salts, carboalkoxy with 2 to 9 carbon atoms, aminocarbonyl, monoalkylaminocarbonyl or dialkylaminocarbonyl with 1 to 4 carbon atoms per alkyl part or nitrile, $R_6$ is selected from the group consisting of hydrogen, sulphonic acid or its salts, chlorine, alkyl with 1 to 4 carbon atoms or alkoxy with 1 to 4 carbon atoms and M is a salt-forming cation.

5. Distyryl-dibenzofuranes according to claim 1, corresponding to the formula

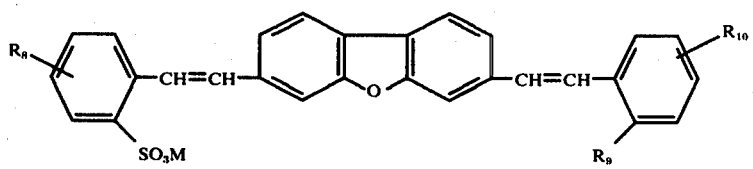

wherein $R_8$ is hydrogen, chlorine, methyl or methoxy, $R_9$ represents hydrogen, the sulphonic acid group or its salts, chlorine, methyl or methoxy, $R_{10}$ is hydrogen, chlorine, methyl or methoxy and M is a salt-forming cation.

6. Organic materials of polyamides and cellulose, containing 0.0001 to 1 percent by weight, calculated relative to the total amount of organic material, of at least one of the distyryl-dibenzofurane compounds as defined in claim 1.

7. Washing agent for textile organic materials of polyamides and celluloses, which contains 0.01 to 2 percent by weight of at least one distyryl-dibenzofurane compound, as defined in claim 1.

8. A process for the optical brightening of organic materials selected from the group consisting of polyamides and celluloses, wherein the improvement comprises incorporating into said materials to be optically brightened or applying to the surface of said materials to be optically brightened effective amounts of distyryl-dibenzofurance compounds of claim 1.

* * * * *

UNITED STATES PATENT OFFICE
CERTIFICATE OF CORRECTION

PATENT NO. : 4,016,156
DATED : April 5, 1977
INVENTOR(S) : Kurt Weber et al.

It is certified that error appears in the above–identified patent and that said Letters Patent are hereby corrected as shown below:

Column 20, claim 1, line 38, delete "or" and insert --- of ---.

Signed and Sealed this nineteenth Day of July 1977

[SEAL]

Attest:

RUTH C. MASON
Attesting Officer

C. MARSHALL DANN
Commissioner of Patents and Trademarks